United States Patent [19]

Koeniger

[11] 4,449,257

[45] May 22, 1984

[54] INTRAOCULAR LENS AND METHOD OF RETAINING IN PLACE

[75] Inventor: Erich A. Koeniger, Metairie, La.

[73] Assignee: Barnes-Hind/Hydrocurve, Inc., Sunnyvale, Calif.

[21] Appl. No.: 373,935

[22] Filed: May 3, 1982

[51] Int. Cl.³ .................... A61F 1/16; A61F 1/24
[52] U.S. Cl. .................................................. 3/13
[58] Field of Search ....................................... 3/13, 1

[56] References Cited

U.S. PATENT DOCUMENTS

| | | | |
|---|---|---|---|
| 3,760,045 | 9/1973 | Thiele et al. | 3/13 X |
| 3,913,148 | 10/1975 | Potthast | 3/13 |
| 3,961,379 | 6/1976 | Highgate | 3/13 |
| 4,242,762 | 1/1981 | Tennant | 3/13 |
| 4,244,060 | 1/1981 | Hoffer | 3/13 |
| 4,254,509 | 3/1981 | Tennant | 3/13 |
| 4,254,510 | 3/1981 | Tennant | 3/13 |

FOREIGN PATENT DOCUMENTS 2071352 9/1981 United Kingdom ................ 3/13

OTHER PUBLICATIONS

"Intra-Ocular Acrylic Lenses After Cataract Extraction", by Harold Ridley et al., The Lancet, Jan. 19, 1952, pp. 118-121.

Primary Examiner—Ronald L. Frinks

[57] ABSTRACT

An intraocular lens of HEMA plastic cut while hard into a round lens with concentric grooves around peripheral margins. The lens is cut to a size that is small for emplacing but softens and expands to fill a posterior chamber capsule after it has been emptied of its natural contents. The softening and expanding of the lens is caused by the aqueous humor uptake into the of the dry lens from the capsule environment. The concentric grooves frictionally engage the rough interior walls of the said capsule to position and retain the lens in place therein.

5 Claims, 3 Drawing Figures

INTRAOCULAR LENS AND METHOD OF RETAINING IN PLACE

BACKGROUND OF THE INVENTION

The invention relates generally to intraocular lenses and more particularly to a soft intraocular lens and method of retaining in a posterior chamber capsule.

The prior art teaches hard PMMA or glass intraocular lenses that are held in place in the posterior chamber with loops, clips, staves and sutures Excerpts from the current Ophthalmology Times issues of July and October of 1981 are enclosed.

The invention teaches a soft HEMA plastic lens that is cut and shaped when dry to a shape that will expand and soften with the uptake of aqueous humor in the eye to fill the posterior capsule of the posterior chamber and be held in place therein by concentric grooves cut in the marginal peripheral area to frictionally engage rough interior surfaces of the capsule.

SUMMARY OF THE INVENTION

It is an object of the invention to provide a soft intraocular lens for placing in the capsule of the posterior chamber while hard that will soften and expand to fill the capsule.

Another object of the invention is to cut concentric grooves around the peripheral marginal areas of a lens when hard that will frictionally engage rough inner surfaces of capsule inner surfaces when the lens softens and expands to fill the capsule on uptake of aqueous humor in the eye.

DETAILED DESCRIPTION OF THE PREFERRED EMBODIMENT

Figure 1:
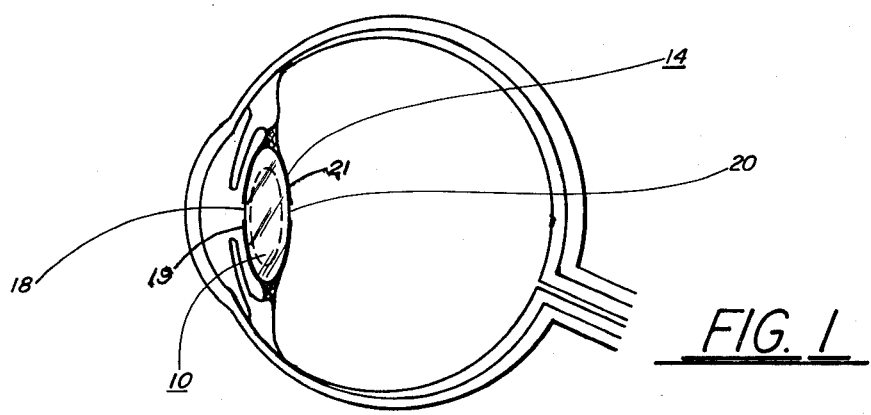
FIG. 1 is a vertical cross-section of an eye showing the lens of the invention operably in place dry and after aqueous humor uptake.
Figure 2:
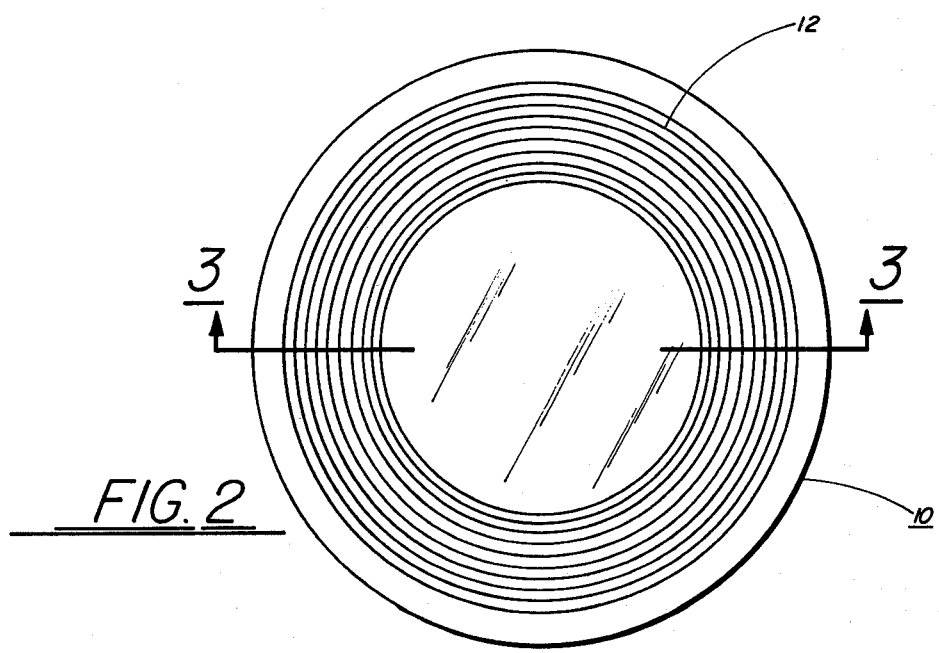
FIG. 2 is a plan view of the invention.
Figure 3:
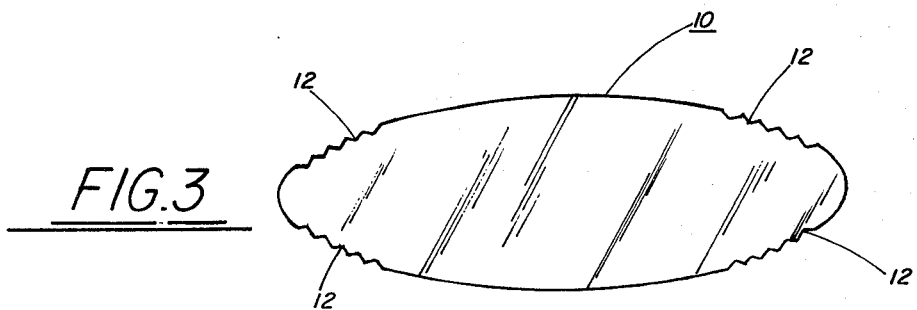
FIG. 3 is a side view of the invention.

Referring to FIGS. 1-3, the lens 10 of the invention comprises a lens made of soft material, HEMA, with a water uptake of 45%, 55%, or 70%, whichever is best suited to the comfort of the patient. The lens is round with concentric grooves 12 cut into marginal peripheral areas on both sides of the lens. The cutting and shaping of the lens 10 is done with dry HEMA, and at a reduction in size, proportional to expansion of the type of HEMA used after water uptake, of the desired size that is to fill the capsule 14 of the posterior chamber 16 (see FIG. 1) as shown in full lines. The lens is inserted dry through a hole 18 trephined in the center of the anterior wall 19 of the capsule 14. Uptake of aqueous humor of the eye softens and expands lens 10 from its original insertion size as shown in broken lines to fill the capsule 14. Grooves 12 frictionally engage the inside walls of the capsule that are naturally rough to firmly hold the lens in place without any clips, loops, and/or staves and sutures (not shown). A hole 20 is also trephined in the center of posterior wall 21 to allow for the passage of light through the lens to the retina of the eye. Posterior holes 18 and 20 are respectively 5 to 6 mm. and 3 to 4 mm. in diameter.

If the lens should for any reason become dislodged, no damage to the retina should occur because the lens is round, soft and has no clips or loops or other external apparatus for holding the lens in position.

Additionally the lens of the invention with aspheric design is usable to correct myopia and hypeopia in the method described above in a better optical solution to restore sight than radial keratotomy. It is much safer to restore a patient's vision by implanting a soft intraocular lens than by cutting the cornea radially.

What is claimed is:

1. An intraocular lens for placing in a posterior chamber capsule and comprising:
   (a) plastic HEMA circular body means for emplacement when dry and contracted, and to expand in place when softened by acqueous humor uptake of the environment; and
   (b) concentric groove means defined around peripheral margins on both sides of said body means for frictionally engaging the interior walls of said posterior capsule.

2. An intraocular lens as described in claim 1 wherein said plastic HEMA circular body means comprises a HEMA with 45% liquid uptake.

3. An intraocular lens as described in claim 1 wherein said plastic HEMA circular body means comprises a HEMA with 55% liquid uptake.

4. An intraocular lens as described in claim 1 wherein said plastic HEMA circular body means comprises a HEMA with 75% liquid uptake.

5. Method of retaining an intraocular lens in a posterior chamber capsule comprising the steps of:
   (a) trephining a hole in the anterior wall of the posterior chamber capsule;
   (b) removing natural contents of said posterior chamber capsule;
   (c) trephining a hole in the posterior wall of said capsule;
   (d) cutting a dry contracted circular lens to a size that expands on acqueous humor uptake to fill said posterior capsule;
   (e) cutting concentric grooves in said dry lens' peripheral margins for frictionally engaging said capsule walls;
   (f) inserting dry and contracted lens through said anterior wall hole into said posterior chamber capsule; and
   (g) allowing dry and contracted lens to soften and expand for positioning it in said posterior chamber capsule to engage said capsule interior walls with said concentrically grooved peripheral margins.

* * * * *